(12) United States Patent
Mitsui

(10) Patent No.: US 7,427,273 B2
(45) Date of Patent: Sep. 23, 2008

(54) SKIN BEAUTIFICATION COSMETIC SYSTEM USING IONTOPHORESIS DEVICE, ULTRASONIC FACIAL STIMULATOR, AND COSMETIC ADDITIVE

(75) Inventor: Yukio Mitsui, Tokorozawa (JP)

(73) Assignee: Japan Natural Laboratory Co., Ltd., Saitama-ken (JP)

( * ) Notice: Subject to any disclaimer, the term of this patent is extended or adjusted under 35 U.S.C. 154(b) by 0 days.

(21) Appl. No.: 11/067,902

(22) Filed: Mar. 1, 2005

(65) Prior Publication Data

US 2005/0191252 A1 Sep. 1, 2005

(30) Foreign Application Priority Data

Mar. 1, 2004 (JP) ............................. 2004-056495

(51) Int. Cl.
*A61H 1/00* (2006.01)
(52) U.S. Cl. ............................................. 601/2; 601/17
(58) Field of Classification Search ............ 604/20–21, 604/65–66; 601/2, 17
See application file for complete search history.

(56) References Cited

U.S. PATENT DOCUMENTS

| | | | |
|---|---|---|---|
| 5,667,487 A * | 9/1997 | Henley | ........................ 604/20 |
| 6,643,544 B1 | 11/2003 | Adachi et al. | |
| 6,743,215 B2 | 6/2004 | Bernabei | |
| 6,743,779 B1 | 6/2004 | Unger et al. | |
| 6,792,306 B2 * | 9/2004 | Henley et al. | ................ 604/20 |
| 2003/0211183 A1 * | 11/2003 | Takahashi et al. | ........... 424/770 |
| 2004/0010222 A1 * | 1/2004 | Nunomura et al. | ............ 604/22 |
| 2005/0043654 A1 * | 2/2005 | Matsumura et al. | ............ 601/2 |

\* cited by examiner

*Primary Examiner*—Michael A. Brown
(74) *Attorney, Agent, or Firm*—Cermak Kenealy & Vaidya LLP

(57) ABSTRACT

A skin beautification cosmetic system comprising an iontophoresis device, an infrared (including far infrared) generator, an ultrasonic vibrator, and a cosmetic composition is disclosed. The system ensures effective action of moisturizing and whitening cosmetics without causing any problem in the skin. By specifying the type of cosmetic to be used, the system can ensure a more effective beautification action, can improve dry skin and aging skin which adversely affect the female skin, and can decompose and remove melanin. Moisturizing and/or whitening cosmetic components such as hydrophilic gel and ultrafine gel are applied to the face or skin or impregnated in a skin contact member section, following which iontophoresis high frequency vibration is applied to the face or skin for a prescribed period of time using an ultrasonic vibrator 3 with built-in high ionization iontophoresis device 2 and infrared generator 9.

15 Claims, 7 Drawing Sheets

(A)

(B)

(A)

(B)

Change in the amount of vitamin C osmosis in to dermis and epidermis of rat by simple external application of vitamin C.

Change in the amount of vitamin C osmosis into dermis and epidermis of rat by iontophoresis application of vitamin C.

Fig. 6

<Simple external application>

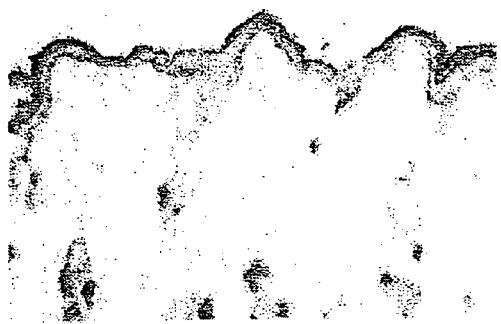

Control

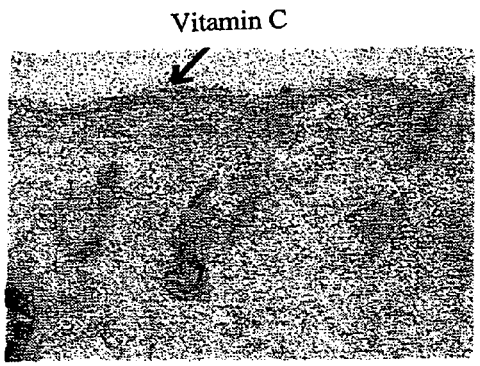

One hour after simple external application
vitamin C was confirmed in epidermis.

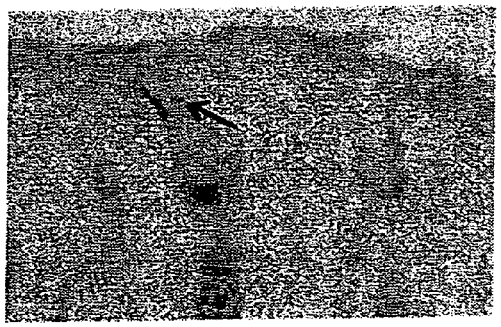

Two hours after simple external application
Some amount of Vitamin C penetration around
the hair root can be seen.

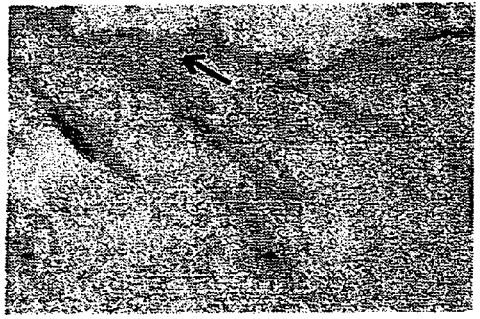

Four hours after simple external application

Five hours after simple external application
A further increase in the dermis can be seen.

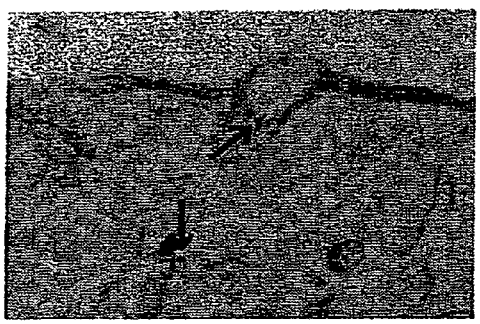

Six hours after simple external application
Abundant Vitamin C penetration in the dermis
and around the hair root can be seen.

Fig. 7

<Iontophoresis application>

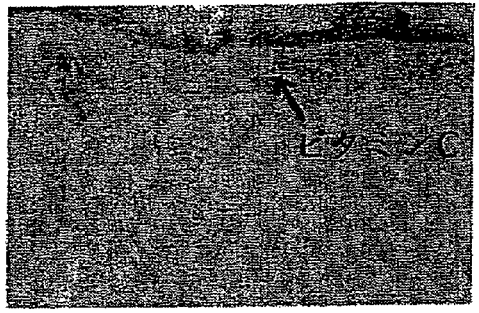

0.5 Hour after iontophoresis application
A larger amount of vitamin C penetration
as compared with simple external application
can be seen.

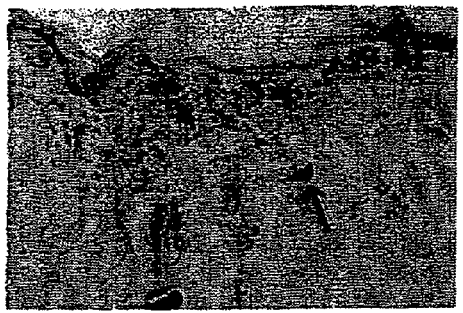

One hour after iontophoresis application
A larger amount of vitamin C penetration
can be seen in the dermis.

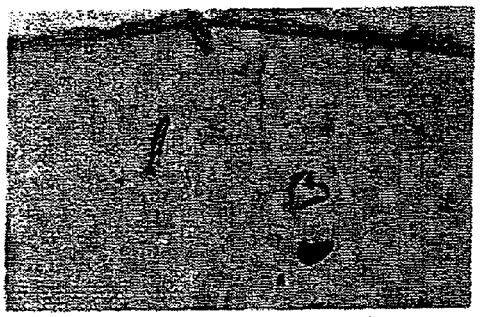

Three hours after iontophoresis application
Vitamin C is confirmed to have reached
the dermis, although the amount is smaller than
the amount after one hour. Vitamin C has been
effectively utilized by cells and disappeared.

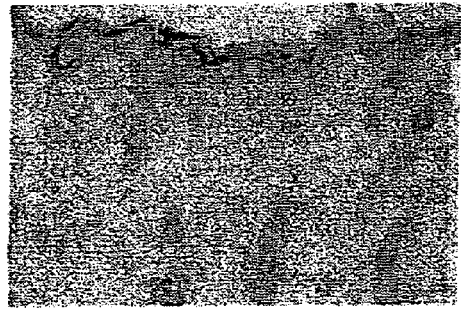

Four hours after iontophoresis application
Vitamin C is gradually disappearing due
to utilization by cells.

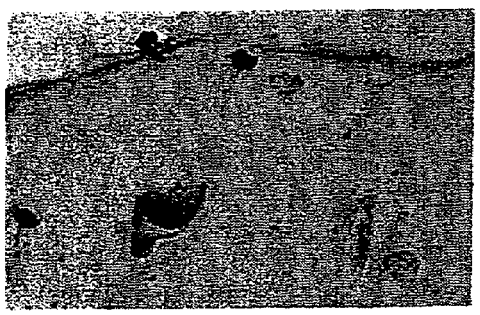

Six hours after iontophoresis application
Efficient vitamin C penetration in the dermis can be seen.

SKIN BEAUTIFICATION COSMETIC SYSTEM USING IONTOPHORESIS DEVICE, ULTRASONIC FACIAL STIMULATOR, AND COSMETIC ADDITIVE

This invention claims the benefit of Japanese patent application No. 2004-56495, filed on Mar. 1, 2004, which is hereby incorporated by reference.

BACKGROUND OF THE INVENTION

1. Field of the Invention

The present invention relates to an ultrasonic skin beautification cosmetic system and, more particularly, to a skin beautification cosmetic system comprising a handy ultrasonic vibrator with an iontophoretic function that can provide a beautification action in a safe manner and a cosmetic additive.

2. Description of the Related Art

In recent years, there is a very high concern about cosmetics regardless of age or sex. In particular, in pursuit of a measure to increase an effect of a cosmetic composition on the face or a measure to secure safety for the face or skin, in addition to applying cosmetics to the face and skin by hand, the use of instruments such as an iontophoresis device and ultrasonic vibrator to increase efficiency has been studied.

Based on this standpoint, an instrument using an iontophoresis device to accelerate penetration of a cosmetic composition, an instrument using ultrasonic waves to assist absorption of a cosmetic composition into the face and skin by the ultrasonic vibration and the like, and an instrument using ultrasonic waves to clean soiled face and skin by vibration have been developed.

In skin and facial care using ultrasonic vibration, microvibration that cannot be provided by human hands activates the skin by providing the skin with a cleansing effect, removing old keratin, and restoring normal conditions of the skin.

As is well known, skin care using iontophoresis causes vitamins which are scarcely absorbed in the skin by a common external application to become ionized and penetrate into the skin by means of electric current.

However, since the human skin is inherently very delicate, some cosmetic users may develop a rash or itch, or in some cases, may receive more serious damage to the face or skin according to the type of cosmetic composition. The same problems may also happen when using ultrasonic vibrating instruments. Use of these instruments for a long period of time may unknowingly damage the face or skin and cause skin problems.

Japanese Patent Application Laid-open No. 259045/2001, relating to an electronic skin beautifying device and an ion introducing method using the electronic skin beautifying device, has an objective of providing an electronic skin beautifying device which does not cause skin problems even after long-term use and is safe and sufficient and discloses a device having an electrode for introducing ions of effective components for an area of the skin to be treated and an ultrasonic vibrator transducer for imparting ultrasonic vibrations to the area of the skin to be treated via the ion introducing electrode.

Japanese Patent Application Laid-open No. 259045/2001 relates to an electronic skin beautifying device and an ion introducing method using the electronic skin beautifying device, of which the mechanism and system are quite different from those of the present invention.

The present inventor has conducted extensive studies with an objective of developing an electronic skin beautification device which does not cause skin problems and is safe even if used for a long time and provides a sufficient effect in a short period of time. As a result, the inventor has successfully developed an instrument having an ultrasonic vibrator which imparts ultrasonic vibration of a specific wavelength to an area of the skin to be treated. The present invention provides a skin beautification cosmetic system comprising an organic combination of an iontophoresis device, and an ultrasonic vibrator, and a cosmetic additive.

A subject to be solved in the present invention is to remove problems with conventional iontophoresis devices, ultrasonic vibrators, or instruments combining these devices and to provide a system utilizing an organic combination of the iontophoresis device and ultrasonic vibrator with a cosmetic additive to be used, so that an effective action of the cosmetic can be derived and, at the same time, the instruments can be used in a safe manner without causing problems. More specifically, the object of the present invention is to secure safety in the use of the instruments, to ensure a more effective beautification action, to provide improvement of dry skin and aging skin which adversely affect the female skin, and to decompose and remove melanin, all of which have been longstanding problems, by specifying the frequency of the ultrasonic vibrator and, at the same time, specifying antioxidative/antityrosinase cosmetic components which can be ionized as the components to be used in the cosmetic composition with due consideration to mutual reactivity with cosmetic additives such as a moisturizing cosmetic additive (e.g. hydrophilic gel) and/or a whitening cosmetic additive, and in particular, with cosmetic bases.

As a result of extensive studies on the above ultrasonic vibrator, the present inventor has found that if the frequency is specified to a range higher than a certain level, the wave is small and unexpectedly safe to the skin, and if the cosmetic to be used is a combination of a specific cosmetic component such as a moisturizing cosmetic additive and/or whitening cosmetic additive, a cosmetic component such as hydrophilic gel, and an antioxidative/antityrosinase cosmetic component which can be ionized, mutual reactivity with the cosmetic base is excellent, the cosmetic is safe and provided with an outstandingly improved cosmetic function of releasing, decomposing, and excluding proteins by decreasing molecular weight, pulverization, or granulation of melanin, and an excellent skin beautification cosmetic system not affected by light and air can be provided, resulting in a distinct improvement of the beautification effect.

SUMMARY OF THE INVENTION

The above object can be achieved in the present invention by a skin beautification cosmetic system comprising an ultrasonic vibrator using a high frequency, an iontophoresis device, and a cosmetic additive.

In the present invention, the skin beautification cosmetic system comprising a combination of a high frequency ultrasonic vibrator, an iontophoresis device, and a cosmetic additive can synergistically take advantage of the excellent effects of these instruments on the skin, which is further increased by the combination of a cosmetic additive with these instruments.

The object of the present invention can also be achieved by the skin beautification cosmetic system described above, wherein the ultrasonic vibrator contains a high ionization iontophoresis device.

In the present invention, the skin beautification effect is increased by the use of a high ionization iontophoresis device as the iontophoresis device.

The object of the present invention can be further achieved by the skin beautification cosmetic system described above, wherein the cosmetic additive comprises a moisturizing cosmetic additive and/or a whitening cosmetic additive.

In the present invention, the skin beautification effect, including a skin whitening effect, is increased by the use of a moisturizing cosmetic additive and/or a whitening cosmetic additive.

The above object can be further achieved in the present invention by the skin beautification cosmetic system described above, wherein the cosmetic additive comprises a moisturizing cosmetic additive selected from the group consisting of hyaluronic acid, collagen, placental extract, sake lees extract and/or deep seawater sake lees extract, lactic acid, and natural moisturizing agents.

In the present invention, the skin beautification effect, including a skin moisturizing effect, is increased by the use of the specified moisturizing cosmetic additive.

The object of the present invention can also be achieved by the skin beautification cosmetic system described above, wherein a hydroquinone, vitamin C derivative, placental extract, or the like is added as a whitening cosmetic additive.

In the present invention, the skin beautification effect, including the whitening effect, is increased by the use of the specified whitening cosmetic additive. In the present invention, the skin beautification effect is increased by the use of ultrasonic waves that can promote enzyme activities and accelerate conversion of vitamin C derivatives into ascorbic acid.

The object of the present invention can also be achieved by the skin beautification cosmetic system described above, wherein the frequency of the ultrasonic vibrator is in a range of 5-6 MHz.

In the present invention, since the specified high frequency vibration in the range of 5-6 MHz is used in the skin beautification cosmetic system, a more effective action is provided by the vibration, specifically the skin fat is provided with a favorable effect and safety of the skin is ensured by a short wavelength.

The object of the present invention can also be achieved by the skin beautification cosmetic system described above, wherein the cosmetic additive is an ionizable antioxidative/antityrosinase cosmetic composition.

Since the present invention comprises a cosmetic composition such as a gel containing ionizable antioxidative/antityrosinase, in addition to the above features, the cosmetic composition exhibits excellent mutual reactivity with cosmetic bases, is stable, and is not affected by light or air.

The object of the present invention can also be achieved by the skin beautification cosmetic system described above, wherein the cosmetic additive is a hydrophilic gel.

In the present invention, in addition to the above features, since the cosmetic additive is a hydrophilic gel, convection into water by ultrasonic wave is excellent, which ensures cosmetic penetration into the skin by the ultrasonic vibration.

The object of the present invention can also be achieved by the skin beautification cosmetic system described above, wherein the cosmetic additive is an ultrafine particle gel.

In the present invention, in addition to the above features, since the cosmetic component is an ultrafine particle gel referred to as nano-gel, convection into the skin by ultrasonic wave is excellent, which ensures cosmetic penetration into the skin by ultrasonic vibration.

The object of the present invention can also be achieved by the skin beautification cosmetic system described above, comprising an iontophoresis device for high ionization, an ultrasonic vibrator with a frequency of 5-6 MHz, and a hydrophilic gel and/or ultrafine particle gel as a cosmetic additive.

In the present invention, since the specified high frequency vibration in the range of 5-6 MHz is used in the skin beautification cosmetic system, a more effective action is provided by the vibration, specifically the dermal fat is provided with a favorable effect and safety of the skin is ensured by a short wavelength. In addition, the skin beautification effect is increased by using a high ionization iontophoresis device as the iontophoresis device. In addition to the above features, since the cosmetic additive is a hydrophilic gel, convection into water by ultrasonic wave is excellent, which ensures cosmetic penetration into the skin by ultrasonic vibration. Moreover, in addition to the above features, since the cosmetic component is an ultrafine particle gel referred to as nano-gel, convection into the skin by ultrasonic waves is excellent, which ensures cosmetic penetration into the skin by ultrasonic vibration.

The object of the present invention can also be achieved by the skin beautification cosmetic system described above, comprising an iontophoresis device for high ionization, infrared (including far-infrared) generator, an ultrasonic vibrator with a frequency of 5-6 MHz, and a hydrophilic gel and/or ultrafine particle gel as a cosmetic additive.

In the present invention, since the skin beautification cosmetic system is provided with an infrared (including far-infrared) generator in addition to the above features, the system can exhibit a hyperthermia effect, which improves blood circulation and enhances penetration of cosmetic into the skin. Specifically, infrared radiation (including far-infrared radiation) vibrates, resonates, and activates the motion of atoms forming the human body to derive a hyperthermia effect, whereby blood circulation in the body can be promoted and metabolism can be accelerated.

The object of the present invention can also be achieved by the skin beautification cosmetic system described above, wherein the skin beautification effect is obtained by metabolism and fat combustion which are derived from frictional heat with the skin and an increase in basic metabolism due to ultrasonic vibration.

In the present invention, the ultrasonic vibration creates frictional heat with the skin, and the heat penetrates the skin and promotes blood circulation, thereby ensuring fat combustion due to body metabolism and basal metabolism.

The object of the present invention can also be achieved by the skin beautification cosmetic system described above, wherein the ultrasonic vibrator comprises a component for storing and leaching the cosmetic additive.

In the present invention, in addition to the above features, since the ultrasonic vibrator is provided with a component for storing and leaching the cosmetic additive, the operation of applying the cosmetic composition each time the system is used can be omitted.

The object of the present invention can also be achieved by an ultrasonic facial stimulator comprising an ultrasonic vibrator having a high ionization iontophoresis device and an infrared or far-infrared generator.

The above object can further be achieved by the ultrasonic skin stimulator, wherein the frequency of the ultrasonic vibrator is in a range of 5-6 MHz.

BRIEF DESCRIPTION OF THE DRAWINGS

FIG. 6 shows the change over time when vitamin C penetrates from the epidermis into the dermis in the case of simple external application in Test Example 3.

FIG. 7 shows the change over time when vitamin C penetrates from the epidermis into the dermis in the case of iontophoretic application in Test Example 4.

DETAILED DESCRIPTION OF THE INVENTION AND PREFERRED EMBODIMENTS

Preferred embodiments of the present invention will be specifically described below referring to FIGS. 1 and 2. It is to be noted that the embodiments described below are preferred examples with various technical limitations, which are not intended to limit the present invention unless specifically stated that the present invention is limited to a certain distinctly specified feature.

The present invention provides a skin beautification cosmetic system comprising a combination of a handy ultrasonic skin stimulator with an iontophoresis device incorporated therein and moisturizing/whitening cosmetic additives.

As mentioned above, in skin and facial care using ultrasonic vibration, microvibration that cannot be provided by human hands activates the skin by providing the skin with a cleansing effect, removing old keratin, and restoring normal conditions of the skin. It has been known that the ultrasonic vibration creates frictional heat with the skin, and the heat penetrates the skin and promotes blood circulation, thereby ensuring good effects such as metabolism.

As is well known, skin care using iontophoresis causes vitamin C and the like which are scarcely absorbed in the skin by means of an external application to become ionized and penetrate into the skin by means of electric current. Heretofore, components such as a cosmetic composition applied to the surface have remained on the skin surface and do not reach deep into the skin. An iontophoretic method, however, has made it possible for the cosmetic components to penetrate deep into the skin. In addition, the iontophoretic method exhibits an excretory action of unwanted substances from inside of the skin. Specifically, since the ions possessed by the substances in soiled skin can be caused to flow using a direct current, a counter-electrode current is passed through the body to separate the soil from the skin in the iontophoretic method. The object of the present invention can be achieved using this iontophoretic action in combination with the effect of the ultrasonic vibrator.

In the present invention, as mentioned above, the flow of soil is promoted by ionizing the soil using the iontophoresis device. More specifically, ions possessed by the components in liquid cosmetic to be introduced by ionization is caused to flow by a direct current, whereby a counter-electrode current is caused to pass through the body.

Figure 1:
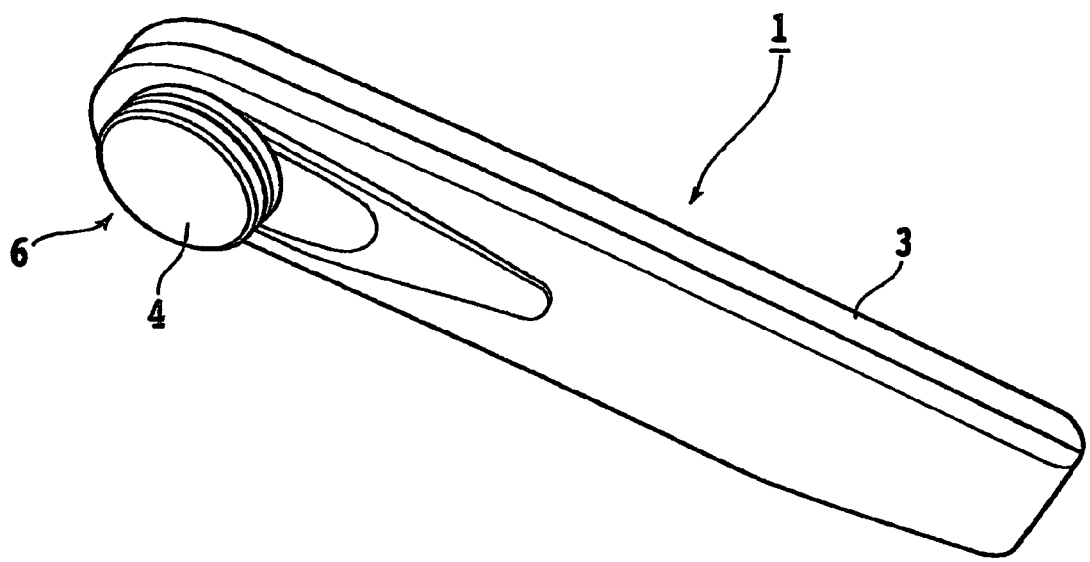
FIG. 1 is a perspective view of an ultrasonic skin stimulator with an iontophoresis device used in the skin beautification cosmetic system of the present invention, wherein (A) shows the side coming into contact with the face and skin and (B) shows the control panel side.
Figure 1:
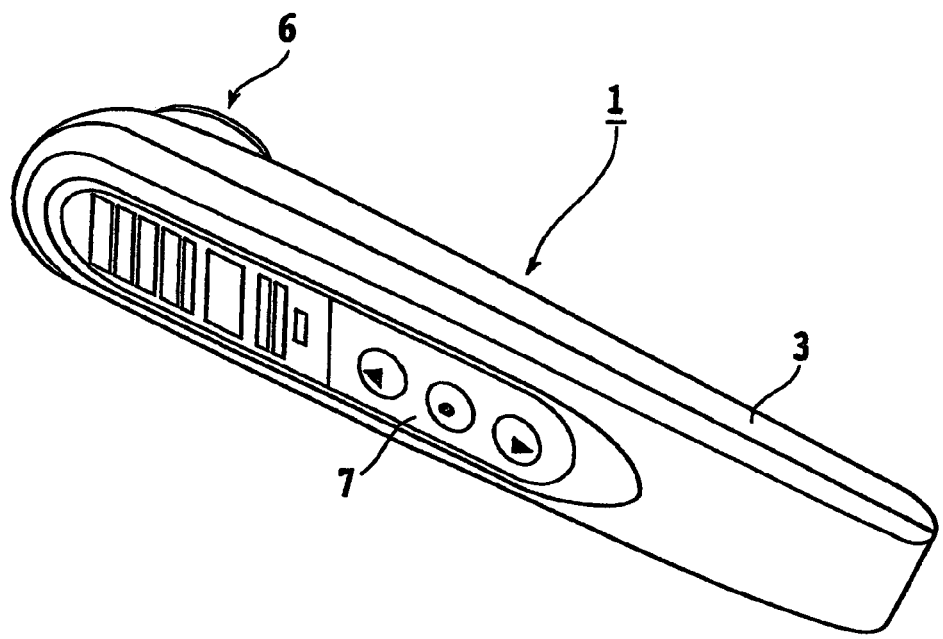

FIG. 1 is a perspective view of an ultrasonic skin stimulator with an iontophoresis device used in the skin beautification cosmetic system of the present invention, wherein (A) shows the side coming into contact with the face and skin and (B) shows the control panel side. In FIG. 1, the numeral 1 indicates a main body of a ultrasonic skin stimulator with an iontophoresis device, 3 indicates a ultrasonic vibrator, and 6 is a head provided at one end of the ultrasonic vibrator 3 which comes in contact with the face and skin to be treated. A moisturizing cosmetic additive, whitening cosmetic additive and the like can be adsorbed in the head 3 and dispensed on use. A pair of electrodes (+ and −) for introducing ion are installed on the head side 6 and the panel side 7, described later, and can be switched by manipulating a switch 4. A control panel 7, provided on one side of the ultrasonic vibrator 3, can set the degree of vibration, the range in number of waves, and the like. A timer and the like may be provided on the control panel 7.

Figure 2:
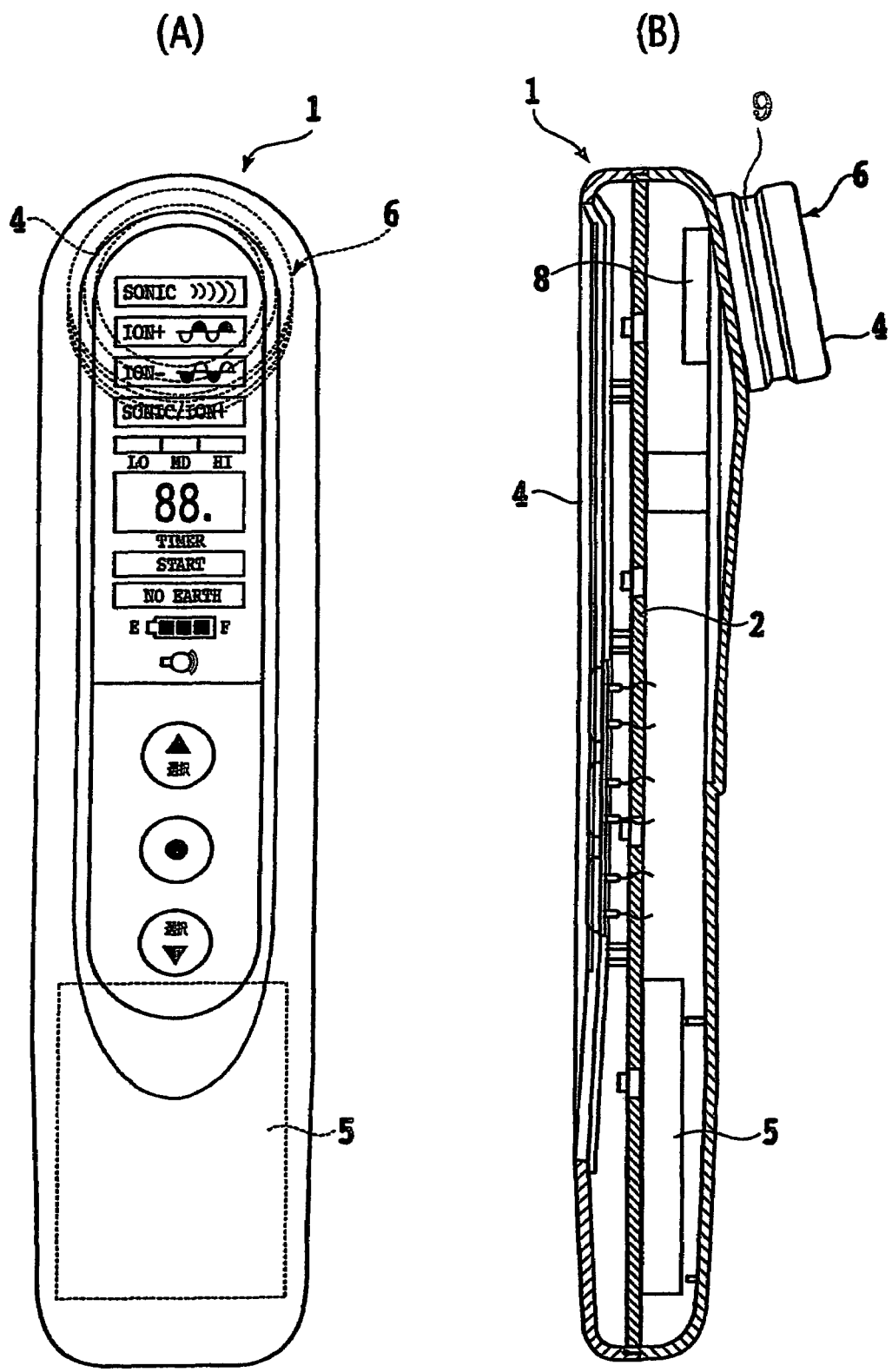
FIG. 2 is a partial broken cross-sectional view of the ultrasonic skin stimulator with an iontophoresis device used in the skin beautification cosmetic system of the present invention, wherein (A) is a front perspective view and (B) is a side cross-sectional view.

FIG. 2 is a cross-sectional view of the ultrasonic skin stimulator with an iontophoresis device used in the skin beautification cosmetic system of the present invention, wherein (A) is a front perspective view and (B) is a side cross-sectional view. In FIG. 2, 2 indicates an iontophoresis device built into the ultrasonic vibrator 3, 4 is an electrode for introducing ions into the iontophoresis device 2, and 5 indicates a power supply source such as an electric cell. A direct current or an alternating current may be used as the power supply 5 instead of an electric cell in business use and the like. A reservoir 8 for cosmetic compositions is provided in the ultrasonic vibrator 3 to release a cosmetic composition during use. 9 indicates an infrared (far-infrared) generator.

Decomposition and exclusion of melanin which are features of the present invention will now be described in detail.

Although melanin plays an important role in shielding the skin from ultraviolet radiation, the melanin causes spots, blotches, and freckles. A compound that can remove these blemishes and prevent their formation is a target of development in the cosmetic industry. Melanin is a high polymer substance. In the skin, melanin bonds with proteins and is present in melanocytes. Nowadays, reducing compounds such as hydroquinones, vitamin C, and its derivatives are used for preventing formation of and removing melanin. However, it is obvious for a person skilled in the art that removing high polymer melanin bonded with proteins is very difficult. Melanin is formed from thyrosin, a type of amino acid, through several process steps in response to the effects of tyrosinase, an enzyme, and ultraviolet radiation. Although the above reducing compounds are effective for causing the reaction products in these steps to be reverted into the product of the previous step, it is well known that once melanin is produced, it cannot be easily reverted to the products in proceeding steps.

The inventor of the present invention has focused an attention to the capability of ultrasonic waves of decomposing and desorbing substances bonded with proteins, pulverizing polymers into fine particles and decreasing the molecular weight of high polymers, as well as the iontophoretic effect of introducing reducing compounds and excretory actions from skin structure, leading to the completion of the present invention. The present invention provides a novel cosmetic (face beautification) method comprising use of a combined ultrasonic-iontophoretic device, use of high frequency which has not been used heretofore, and a further combination with a moisturizing-whitening cosmetic additive, to achieve an increase in a cosmetic effect, safe use of instruments, and an effect of removing melanin.

EXAMPLES

The present invention is described below by examples, which should not be construed as limiting the present invention.

Example 1

A cosmetic composition comprising a placental extract and a vitamin C derivative, which are moisturizing and whitening cosmetic additives, was applied to the face. The face was then vibrated at a frequency of 5 MHz using the above-described ultrasonic vibrator with a built-in iontophoresis device for high ionization and infrared generator for 15 minutes. This treatment was repeated every day for 30 days.

The experiment confirmed a good effect of the instrument on the skin and an increased synergistic effect.

Example 2

| Raw materials | Amount |
| --- | --- |
| 1. Water | 78.38 |
| 2. BG | 4.00 |
| 3. Glycerol | 4.00 |
| 4. Betaine | 1.00 |
| 5. Pentylene glycol | 1.00 |
| 6. Aminocaproic acid | 0.20 |
| 7. Phenoxy ethanol | 0.30 |
| 8. PEG-20 sorbitan cocoate | 0.50 |
| 9. Carbomer | 0.40 |
| 10. Arginine | 0.40 |
| 11. Xanthan gum | 0.10 |
| 12. Cork tree bark extract | 0.12 |
| 13. Sake-lees extract | 7.00 |
| 14. Placental extract | 2.50 |
| 15. Ascorbyl phosphate Mg | 0.10 |
| Total | 100.00 |

A hydrophilic gel cosmetic composition with the above formulation obtained by adding components at a high concentration, adding a minimal amount of oils, and adding a vitamin C derivative for promoting ionization was applied to the face. The face was then vibrated at a frequency of 5 MHz using the above-described ultrasonic vibrator with a built-in iontophoresis device for high ionization and infrared generator for 15 minutes. This treatment was repeated every day for 30 days.

The experiment confirmed a good effect of the instrument on the skin and an increased synergistic effect. In particular, it can be clearly seen that the osmosis rate of the cosmetic composition into the skin can be increased and melanin can be decomposed and removed.

Example 3

600 ml of 100% ethanol was added to 200 g of deep sea water sake lees (manufactured by Hokusetsu Shuzo Co., Ltd., Niigata Prefecture; deep sea water was collected at around 1,000-4,000 m (preferably 2,000-3,000 m) offshore south of Sado Island, Niigata Prefecture, from an ocean depth of 250-500 m (optimum depth: 300-400 m). The mixture was allowed to stand at room temperature for six days while intermittently stirring to obtain an extract. The extract was filtered and the filtrate was concentrated under reduced pressure. 30 ml of ion-exchange water was added to the residue to separate an oil. The oil was extracted twice with 50 ml of ethyl acetate. The resulting aqueous solution was concentrated under reduced pressure to obtain 5 g of syrup.

The sake lees extract obtained by the above procedure and/or deep sea water sake lees extract (hereinafter referred to as "Horus Sake Lees Extract; Oryza Sativa [Sake] Lees Extract") were added to and mixed with the following cosmetic components. A face lotion excelling in an SOD-like activity effect and a tyrosinase inhibitory effect was obtained.

| Raw materials | Amount |
| --- | --- |
| 1. Water | 81.75 |
| 2. Glycerol | 5.00 |
| 3. BG | 5.00 |
| 4. Ascorbyl phosphate Mg | 1.00 |
| 5. Placental extract | 1.00 |
| 6. Sake-lees extract | 2.00 |
| 7. Umbilical extract | 1.00 |
| 8. *Scutellaria* root extract | 0.10 |
| 9. *Angelica keiskei* extract | 0.10 |
| 10. Mulberry bark extract | 0.10 |
| 11. *Aloe vera* extract | 0.10 |
| 12. Dipotassium glycyrrhizate | 0.10 |
| 13. Disodium phosphate | 0.20 |
| 14. Sodium phosphate | 0.05 |
| 15. Phenoxy ethanol | 0.50 |
| 16. Ethanol | 2.00 |
| Total | 100.00 |

The head of the above-described ultrasonic vibrator with a built-in iontophoresis device for high ionization and infrared generator was impregnated with the face lotion containing the deep sea water sake-lees extract and applied to the face. The face was then vibrated at a frequency of 5 MHz for 15 minutes. This treatment was repeated every day for 30 days.

The experiment confirmed a good effect of the instrument on the skin and an increased synergistic effect. In particular, it can be seen clearly that the osmosis rate of the cosmetic composition into the skin can be increased and melanin can be decomposed and removed.

Test Example 1

The test results of vitamin C osmosis into the human skin will be described below.

<Site>Thigh

<Experiment Procedure>

(1) Vitamin C was iontophoretically introduced for five minutes.

(2) After five hours, 5 mm of the skin was punched, separated into epidermis and dermis, and freeze dried.

(3) The Vitamin C concentration in the epidermis and dermis was determined by HPLC.

1) The freeze dry samples were dissolved in 500 □1 of a moving layer solvent.

2) The solution was ultrasonically treated for 10 minutes, 3) filtered through a 0.2 mm filter, and 4) subjected to HPLC measurement.

<Measurement Conditions>

Moving layer: A 0.08 M $CH_3COOH$—$CH_3COONa$ buffer solution (pH 5.0) containing 2.8 mM Mn-hexyl amine, 0.1 mM disodium edetate, and 2% methanol.

Measuring amount: 20 □1

Flow rate: 0.8 ml/min.

Wavelength: 254 nm

Column: ODS column oven: 40° C.

<Results>

|  | Epidermis (ppm) | Dermis (ppm) |
|---|---|---|
| Ascorbic acid | 0.02 | 0.05 |
| L-Ascorbyl phosphate Mg | 0.43 | 0.40 |

<Discussion>

In the dermis, ascorbic acid slightly increased and the derivatives decreased. However, since the total amount did not change, the derivatives are supposed to have changed into ascorbic acid in the dermis catalyzed by enzymes.

In regard to the relationship with the ultrasonic facial stimulator, it can be supposed that enzyme activities are promoted by the use of ultrasonic waves and the enzyme accelerates conversion of vitamin C derivatives into ascorbic acid.

Test Example 2

The test results of collagen synthesis promotion activity of vitamin C will be described below.

<Test Method>

Vitamin C was iontophoretically introduced every day into mice for two weeks and humans for three months. The skin tissues were collected to determine the amount of collagen. For a blank test, the same sites of mice and humans without iontophoretic introduction were used. The following three samples were used in the test.

(1) Rat abdomen
(2) Human face (those with solar elastosis)
(3) Human arm

<Test Results>

Figure 3:
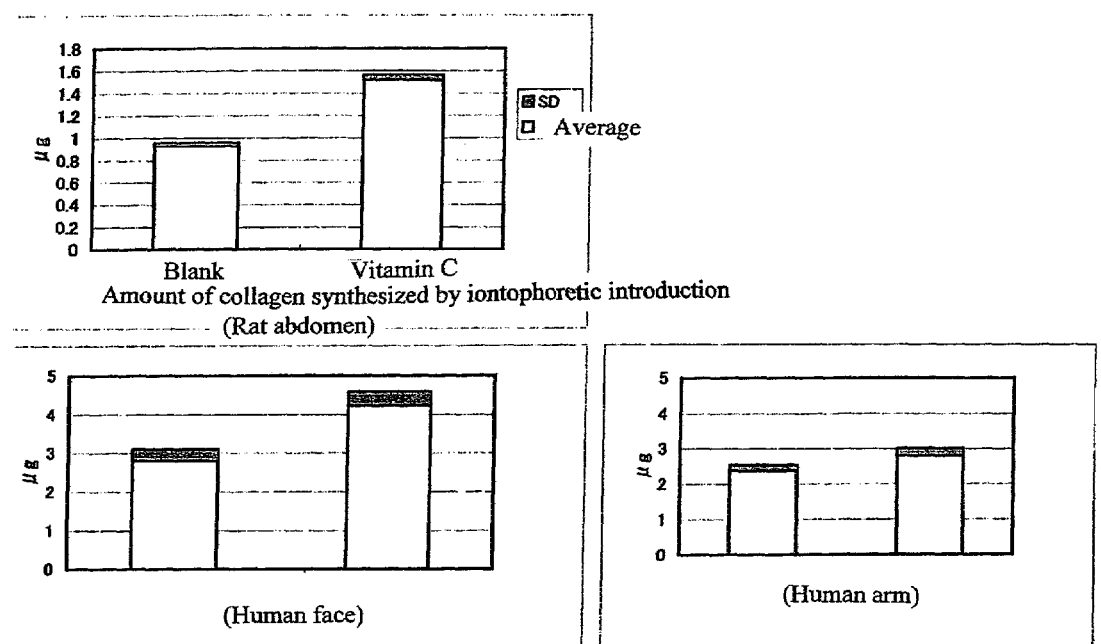
FIG. 3 shows graphs of the change in the amount of collagen after iontophoretic introduction into a solution containing vitamin C or a blank solution in Test Example 2.

The changes in the amount of collagen in solutions containing vitamin C or a blank solution after iontophoretic introduction are shown in FIG. 3.

In all cases, the amount of collagen synthesis was shown to significantly increase by iontophoretic introduction into solutions containing vitamin C.

Test Example 3

There have been almost no actual basic data for iontophoresis of vitamin C which is one type of drug delivery system to accelerate percutaneous absorption compared with simple external application.

The present inventor introduced a 0.1% diluted solution of C-ascorbic acid (hereinafter referred to as Vitamin C) into the back skin of a rat by simple external application and iontophoresis to compare osmosis of vitamin C using a scintillation counter and autoradiography.

<Method>

A 0.1% vitamin C solution was applied to the back skin of a hairless rat for 20 seconds by iontophoresis or for 10 minutes by simple external application. Tissue samples were collected at prescribed intervals (Samples of iontophoresis application: control, 0.5 h, 1 h, 2 h, 3 h, and 6 h; samples of simple external application: control, 1 h, 2 h, 3 h, and 6 h). Each collected sample was cut into two pieces, one of which was separated into epidermis and dermis for use as a scintillation counter sample. A lyophilized section was prepared from the other piece of the sample and developed for autoradiography analysis. The vitamin C concentration in each tissue was determined using IR analysis.

<Results>

Figure 4:
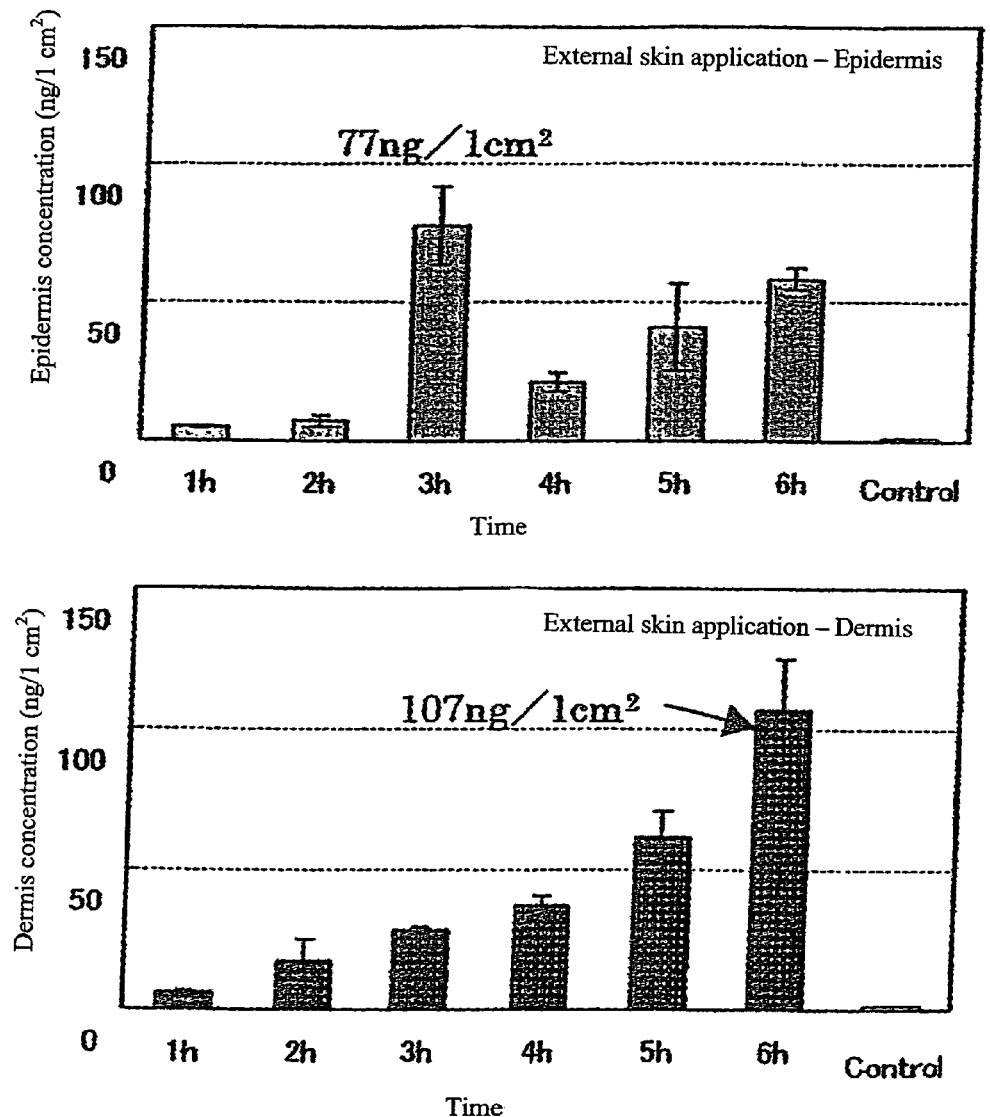
FIG. 4 shows graphs for comparing vitamin C osmosis using a scintillation counter in Test Example 3.
Figure 5:
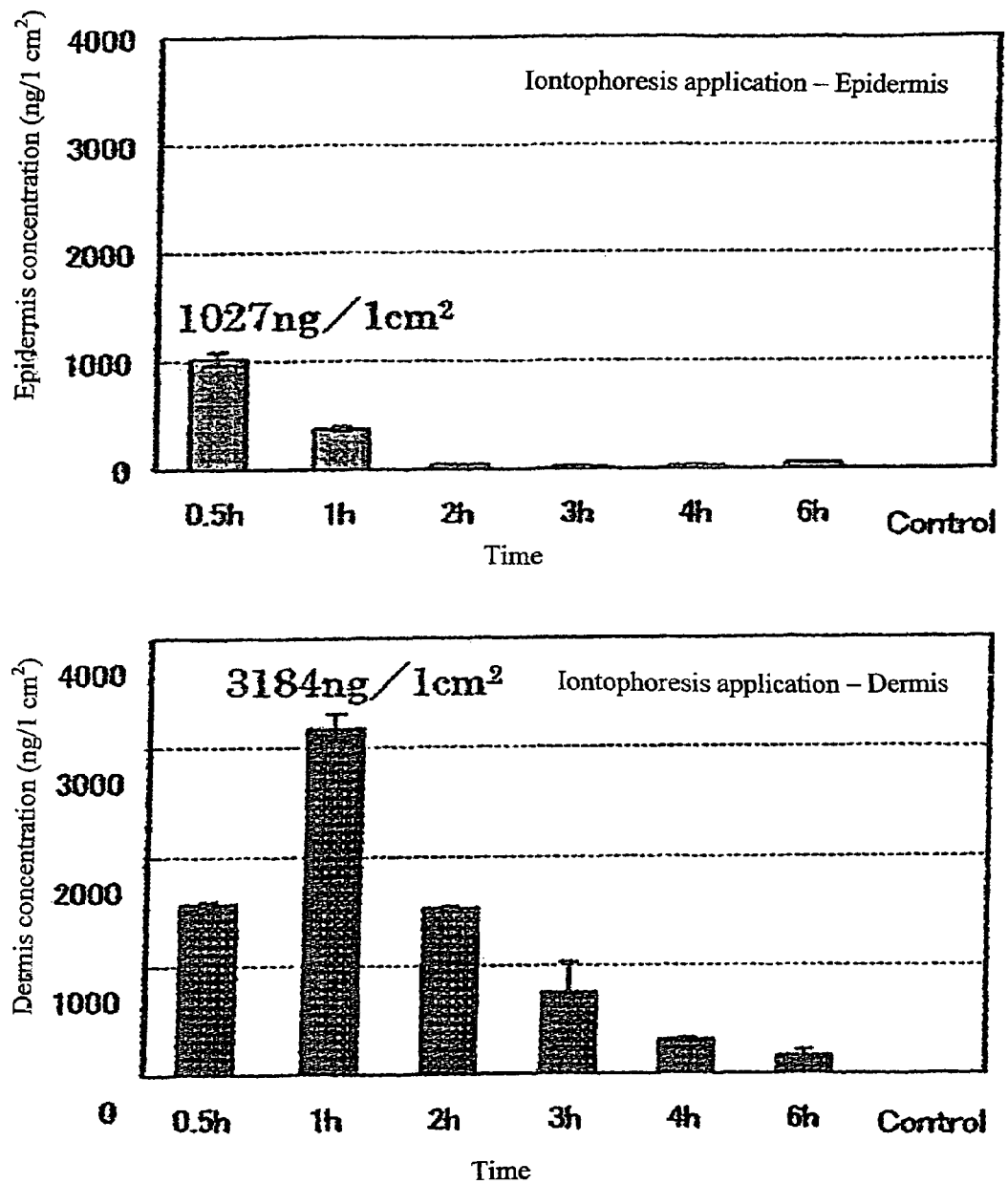
FIG. 5 shows graphs for comparing vitamin C osmosis using a scintillation counter in Test Example 3.

Vitamin C osmosis comparison using a scintillation counter (FIGS. 4 and 5).

In the case of epidermis: The concentration reached maximum at 0.5 hour in the iontophoresis application and three hours in the simple external application.

In the case of dermis: The concentration reached maximum at one hour in iontophoresis application and six hours in simple external application. The osmosis by the iontophoresis application was about 30 times greater than the osmosis by the simple external application.

Vitamin C osmosis comparison using autoradiography.

In the case of simple external application: Vitamine C progressively penetrated from the epidermis into the dermis over time (FIG. 6).

In the case of iontophoresis application: Vitamine C started to penetrate at 0.5 hour and more abundantly after one hour (FIG. 7).

These figures (photographs) display a cross-section of rat skin tissue, wherein black dots in the epidermis and dermis indicate vitamin C.

CONCLUSIONS

Although water-soluble vitamin C permeated effectively by simple external application, a larger amount of vitamin C was confirmed to permeate in a short period of time when iontophoresis was used. Moreover, the difference in the amount of osmosis in the cases of iontophoresis and simple external application of vitamin C was particularly remarkable in the dermis. The amount of osmosises by iontophoresis was about 30 times greater than the osmosis by simple external application.

The above results obtained in the experiment using rats in Test Example 3 easily suggest that the same remarkable effects can be obtained in humans as well.

Although the present invention has been described above as a skin beautification cosmetic system comprising a combination of an ultrasonic vibrator with an iontophoresis device and an infrared generator incorporated therein and moisturizing/whitening cosmetic additives, it is needless to mention that the system can also be used as a medical skin beautification system by using a drug instead of the beautification cosmetic additive.

<Effect of the Invention>

Permeation and absorption of a cosmetic composition such as gel by the skin can be increased by high ionization using ultrasonic waves.

A moisturizing effect can be increased due to the use of a moisturizing cosmetic additive such as hyaluronic acid, collagen, placental extract, sake lees extract and/or deep seawater sake lees extract, lactic acid, and other natural moisturizing agents as a cosmetic additive in combination with the above devices.

A whitening effect can be increased due to the use of a whitening cosmetic additive such as a hydroquinone, a vitamin C derivative, and placental extract in combination with the above devices.

The cosmetic composition exhibits excellent mutual reactivity with cosmetic bases, is highly stable, and has an increased skin beautification effect without being affected by light or air due to the use of an ionizable antioxidative/antityrosinase cosmetic component together with a cosmetic component such as a vitamin C derivative.

The cosmetic composition penetrates well into the skin, exhibits excellent mutual reactivity with cosmetic bases, is highly stable, and has an increased skin beautification effect without being affected by light or air due to the use of a specific cosmetic component such as a hydrophilic gel and ultrafine gel (nano-gel) together with an ultrasonic vibrator.

Since an appropriately high range of frequency is selected, the wavelength of the frequency is short and the skin is protected from being damaged even if an ultrasonic vibrator is used for a long period of time. Moreover, microvibration of five million per second used in the present invention ensures an effect of stimulating the muscles deep in the skin structure and regaining tension and elasticity of the skin which cannot be achieved by massaging with human hands. Furthermore, although loose skin is a cause of degradation of a regenerative function of collagen/elastin used as the source of tension of the skin, in the same manner as in the cause of wrinkles, the system of the present invention can provide highly adsorptive skin with high quality collagen/elastin, which increases tension of the skin and exhibits an effect of lifting the face line and cheek.

The system of the present invention can massage skin cells by ultrasonic waves producing microvibration and has an effect of improving spots and dullness. The spot and dullness improving effects can be brought about by blood circulation promotion due to the metabolism facilitating effect and hyperthermia effect of ultrasonic waves.

Furthermore, the present invention restores tension of the skin and provides a wrinkle improving effect due to ultrasonic waves creating micro vibration which is absorbed in the skin, brings about a hyperthermia effect, promotes blood circulation, acts on the dermal layer, improves flow of lymphs, supplies sufficient oxygen and nutrients, rejects activated oxygen, and stimulates muscles.

Moreover, the present invention is effective in returning a turnover to normal conditions by causing soils entered into pores, old keratin, melanin, pigment, and the like to float due to the vibration effect of the ultrasonic wave which produce microvibration.

Since an appropriately high range of frequency is selected, a high frequency wave number provides a good effect on the dermal fat.

Moreover, the addition of a vitamin C derivative which is easily ionized ensures the cosmetic composition to penetrate into and be absorbed by the skin, whereby the effect of the skin beautification cosmetic system of the present invention is increased.

In addition, break-down, pulverization, and granulation of high molecular weight proteins into low molecular weight compounds by high frequency ultrasonic wave results in exfoliation, fracture, decomposition, and absorption of melanin, whereby whitening of the face or skin can be ensured.

In the present invention, high frequency ultrasonic wave and ultrasonic vibration create frictional heat with the skin, and the heat penetrates the skin and promotes blood circulation, thereby ensuring fat combustion due to body metabolism and basal metabolism.

In the present invention, since the system is provided with an infrared (including far-infrared) generator, the system can exhibit a hyperthermia effect, which improves blood circulation and enhances penetration of cosmetic into the skin.

The skin beautification cosmetic system of the present invention can be used as a simple household skin beautification cosmetic system used in combination with cosmetics for beautifying the face and skin, as a commercial system skin beautification cosmetic system used in combination with cosmetics, and as a medical skin beautification system used in combination with a medicine.

Obviously, numerous modifications and variations of the present invention are possible in light of the above teachings. It is therefore to be understood that, within the scope of the appended claims, the invention may be practiced otherwise than as specifically described herein.

What is claimed is:

1. A skin beautification cosmetic system comprising:
an ultrasonic vibrator using high frequency, an iontophoresis device, and a cosmetic additive, wherein the cosmetic additive includes a moisturizing cosmetic additive selected from the group consisting of hyaluronic acid, collagen, placental extract, sake lees extract and/or deep seawater sake lees extract, and lactic acid, and wherein the frequency of the ultrasonic vibrator is in a range of 5-6 MHz.

2. The skin beautification cosmetic system according to claim 1, wherein the ultrasonic vibrator contains a high ionization iontophoresis device.

3. The skin beautification cosmetic system according to claim 1, wherein the cosmetic additive includes a whitening cosmetic additive.

4. The skin beautification cosmetic system according to claim 1, wherein the whitening cosmetic additive includes at least one of a hydroquinone, a vitamin C derivative, and a placental extract.

5. A skin beautification cosmetic system, comprising:
an ultrasonic vibrator using high frequency,
an iontophoresis device, and
a cosmetic additive wherein the cosmetic additive is an ionizable antioxidative/antityrosinase cosmetic composition.

6. The skin beautification cosmetic system according to claim 1, wherein the cosmetic additive is a hydrophilic gel.

7. The skin beautification cosmetic system according to claim 1, wherein the cosmetic additive is an ultrafine particle gel.

8. The skin beautification cosmetic system according to claim 1, comprising an iontophoresis device for high ionization, an ultrasonic vibrator with a frequency of 5-6 MHz, and a hydrophilic gel and/or ultrafine particle gel as a cosmetic additive.

9. The skin beautification cosmetic system according to claim 1, comprising:
an iontophoresis device for high ionization;
an infrared including far-infrared generator;
an ultrasonic vibrator with a frequency of 5-6 MHz; and
a hydrophilic gel and/or ultrafine particle gel as a cosmetic additive.

10. The skin beautification cosmetic system according to claim 1, wherein the skin beautification effect is obtained by metabolism and fat combustion which are derived from skin frictional heat and an increase in basic metabolism due to ultrasonic vibration.

11. The skin beautification cosmetic system according to claim 1, wherein the ultrasonic vibrator comprises a component for storing and leaching the cosmetic additive.

12. An ultrasonic facial stimulator and skin beautification cosmetic system comprising:
an ultrasonic vibrator having a high ionization iontophoresis device;
an infrared or far-infrared generator; and
a cosmetic additive, wherein the cosmetic additive includes a moisturizing cosmetic additive selected from the group consisting of hyaluronic acid, collagen, placental extract, sake lees extract and/or deep seawater sake lees extract, and lactic acid.

13. The skin beautification cosmetic system according to claim 12, wherein the frequency of the ultrasonic facial stimulator is in a range of 5-6 MHz.

14. The skin beautification cosmetic system according to claim 12, further comprising:
   a cosmetic additive including a moisturizing cosmetic additive selected from the group consisting of hyaluronic acid, collagen, placental extract, sake lees extract and/or deep seawater sake lees extract, and lactic acid.

15. The skin beautification cosmetic system according to claim 12, further comprising:
   a cosmetic additive including an ionizable antioxidative/antityrosinase cosmetic composition.

* * * * *